US010980505B2

(12) United States Patent
Zhang

(10) Patent No.: US 10,980,505 B2
(45) Date of Patent: Apr. 20, 2021

(54) SYSTEM AND METHOD FOR AIR CORRECTION

(71) Applicant: SHANGHAI UNITED IMAGING HEALTHCARE CO., LTD., Shanghai (CN)

(72) Inventor: Dier Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 206 days.

(21) Appl. No.: 16/364,356

(22) Filed: Mar. 26, 2019

(65) Prior Publication Data

US 2019/0216419 A1    Jul. 18, 2019

Related U.S. Application Data

(63) Continuation of application No. PCT/CN2017/092626, filed on Jul. 12, 2017.

(51) Int. Cl.
*G06N 20/00* (2019.01)
*A61B 6/00* (2006.01)
*G06N 3/08* (2006.01)
*G16H 40/40* (2018.01)
*G16H 30/20* (2018.01)
(Continued)

(52) U.S. Cl.
CPC .............. *A61B 6/582* (2013.01); *A61B 6/032* (2013.01); *A61B 6/5205* (2013.01); *G06N 3/08* (2013.01);
(Continued)

(58) Field of Classification Search
CPC ......... G06T 7/0012; G06T 2207/20081; G06T 2207/20084; A61B 6/032; A61B 6/5205;
(Continued)

(56) References Cited

U.S. PATENT DOCUMENTS 4,305,127 A    12/1981  Heuscher
10,445,905 B2 *  10/2019  Wang .................... G06T 11/008
(Continued)

FOREIGN PATENT DOCUMENTS

| CN | 101482971 A | 7/2009 |
| CN | 103134823 A | 6/2013 |
| CN | 106539590 A | 3/2017 |

OTHER PUBLICATIONS

International Search Report in PCT/CN2017/092626 dated Mar. 28, 2018, 4 Pages.
(Continued)

*Primary Examiner* — David P Porta
*Assistant Examiner* — Fani Boosalis
(74) *Attorney, Agent, or Firm* — Metis IP LLC

(57) ABSTRACT

A system and method for air calibration in a Computed Tomography (CT) imaging system are provided. A first set of data associated with air in a scanning area may be obtained. A second set of data associated with an object in the scanning area may be obtained. The second set of data based on the first set of data may be calibrated, and a set of reference values generated by a neural network model may be used to perform the calibration. A third set of data based on the calibration of the second set of data may be generated. Based on the third set of data, a CT image of the object may be generated.

20 Claims, 12 Drawing Sheets

(51) Int. Cl.
*G16H 40/67* (2018.01)
*G16H 30/40* (2018.01)
*G06T 7/00* (2017.01)
*G06T 11/00* (2006.01)
*A61B 6/03* (2006.01)
*G06N 3/04* (2006.01)

(52) U.S. Cl.
CPC ........... *G06N 20/00* (2019.01); *G06T 7/0014* (2013.01); *G06T 11/005* (2013.01); *G16H 30/20* (2018.01); *G16H 30/40* (2018.01); *G16H 40/40* (2018.01); *G16H 40/67* (2018.01); *G06N 3/04* (2013.01); *G06T 2207/10081* (2013.01); *G06T 2207/20081* (2013.01); *G06T 2207/20084* (2013.01)

(58) Field of Classification Search
CPC . A61B 6/582; G06N 3/08; G06N 3/04; G16H 30/20; G16H 30/40; G16H 40/40
See application file for complete search history.

(56) References Cited

U.S. PATENT DOCUMENTS

| | | |
|---|---|---|
| 2013/0156163 A1 | 6/2013 | Liu et al. |
| 2014/0014828 A1 | 1/2014 | Bredno et al. |
| 2015/0170341 A1 | 6/2015 | Fan et al. |
| 2015/0190106 A1 | 7/2015 | Yamakawa et al. |
| 2016/0032395 A1* | 2/2016 | Davicioni ............. G16B 25/00 506/8 |
| 2016/0081643 A1 | 3/2016 | Tsubota et al. |
| 2016/0128782 A1 | 5/2016 | Wei et al. |
| 2016/0143607 A1 | 5/2016 | Cao et al. |
| 2016/0163072 A1 | 6/2016 | Koehler et al. |
| 2016/0239971 A1 | 8/2016 | Yu et al. |
| 2017/0042488 A1 | 2/2017 | Song |
| 2017/0150940 A1 | 6/2017 | Lou et al. |
| 2017/0178366 A1 | 6/2017 | Wang et al. |
| 2018/0144214 A1* | 5/2018 | Hsieh ....................... G06N 3/08 |
| 2018/0161102 A1 | 6/2018 | Wei et al. |
| 2018/0174335 A1 | 6/2018 | Yamakawa et al. |
| 2018/0204305 A1 | 7/2018 | Wang et al. |

OTHER PUBLICATIONS

Written Opinion in PCT/CN2017/092626 dated Mar. 28, 2018, 4 Pages.
First Office Action in Chinese Application No. 201711229793.4 dated Aug. 3, 2020. 12 pages.

* cited by examiner

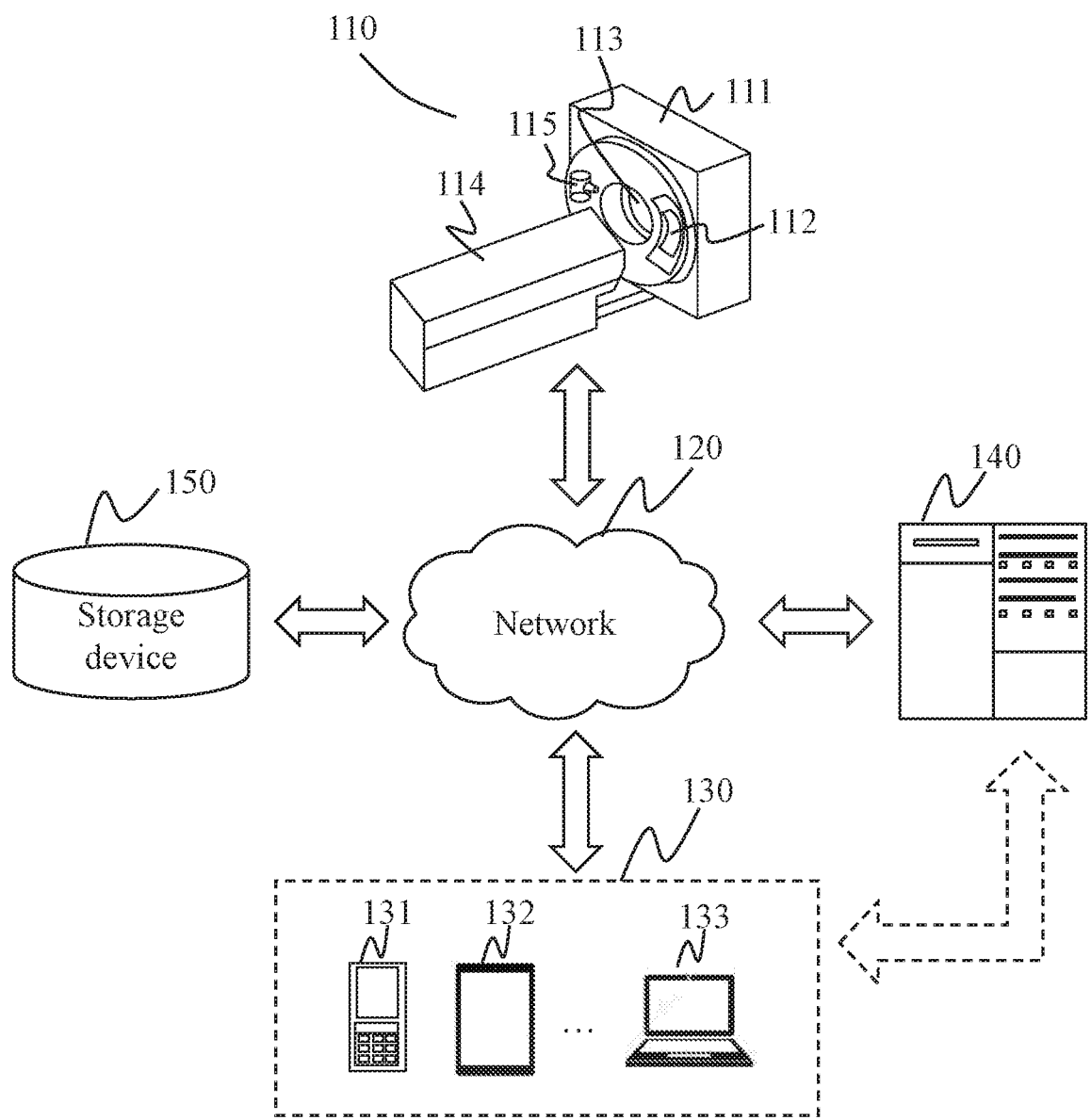
FIG. 1-A

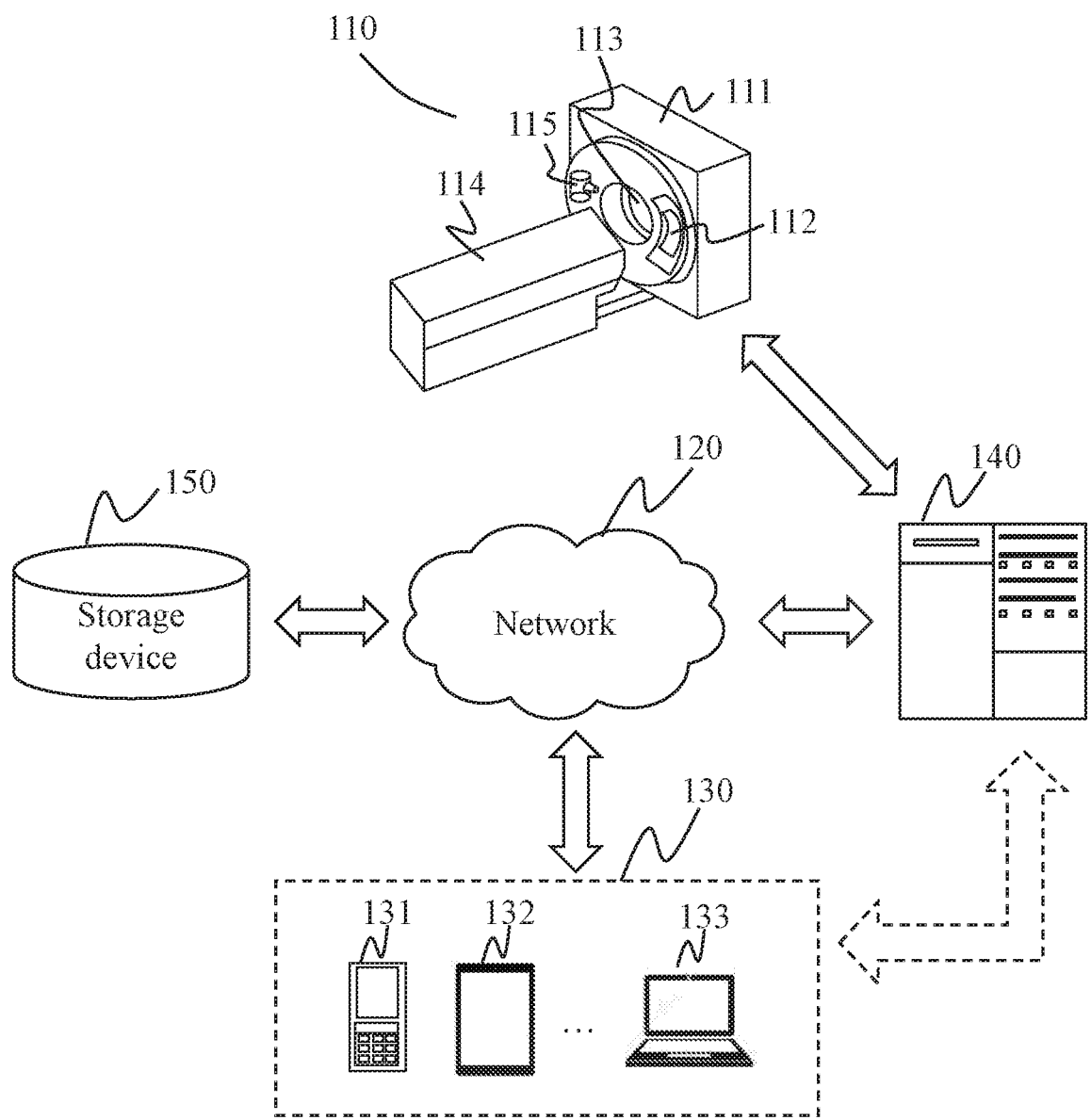
FIG. 1-B

SYSTEM AND METHOD FOR AIR CORRECTION

CROSS-REFERENCE TO RELATED APPLICATIONS

This application is a continuation of International Application No. PCT/CN2017/092626 filed on Jul. 12, 2017, the entire contents of which are hereby incorporated by reference.

TECHNICAL FIELD

The present disclosure generally relates to image reconstruction, and more specifically relates to methods and systems for medical image reconstruction.

BACKGROUND

X-ray computed tomography (CT, Computed Tomography) is commonly used in modern medicine technology. A computed tomography (CT) system may include X-ray tubes and detector arrays that are rotated about a gantry encompassing a subject. The X-ray emitted through the X-ray tubes may be attenuated when going through the subject before it is received by the X-ray detector arrays. The X-ray detector arrays may transform the received X-rays to electrical signals, which may be used to perform an image reconstruction by the CT system.

Air correction may need to be performed on the electrical signals generated by the X-ray detector arrays. In existing technology, a reference detector by the side of the X-ray tube may be used to perform the air correction. However, to deploy a reference detector in the CT system may be cumbersome and the cost is expensive. The recent development of artificial intelligence (AI) may provide a solution in performing the air correction instead of a reference detector.

SUMMARY

In accordance with some embodiments of the disclosed subject matter, a system and methods for air calibration in a Computed Tomography (CT) imaging system are provided.

In accordance with some embodiments of the disclosed subject matter, a method for air calibration may include one or more of the following operations. A first set of data associated with air in a scanning area may be obtained. A second set of data associated with an object in the scanning area may be obtained. The second set of data based on the first set of data may be calibrated, and a set of reference values generated by a neural network model may be used to perform the calibration. A third set of data based on the calibration of the second set of data may be generated. Based on the third set of data, a CT image of the object may be generated.

In some embodiments, the neural network model may include a deep learning neural network model.

In some embodiments, the neural network model may be trained using a plurality of training data associated with at least one detector of the CT imaging system.

In some embodiments, the plurality of training data may be obtained via the at least one detector with respect to a plurality of scanning protocols.

In some embodiments, the neural network model may include at least three layers.

In some embodiments, the set of reference values generated by the neural network model may be view-dependent.

In some embodiments, the set of reference values generated by the neural network model may be slice-dependent.

In some embodiments, the calibrating the second set of data based on the first set of data using a neural network model further include one or more following operations. A slice normalization on the first set of data and the second set of data may be performed. The second set of data based on the first set of data may be calibrated.

Another aspect of the present disclosure relates to a system for air calibration. The system may include a computer-readable storage medium and at least one processor. The computer-readable storage medium may include a first set of instructions for calibrating data. The at least one processor may communicate with the computer-readable storage medium, wherein when executing the first set of instructions, the at least one processor is directed to perform one or more of the following operations. The at least one processor may obtain a first set of data associated with air in a scanning area. The at least one processor may obtain a second set of data associated with an object in the scanning area. The at least one processor may calibrate the second set of data based on the first set of data, and a set of reference values generated by a neural network model is used to perform the calibration. The at least one processor may generate a third set of data based on the calibration of the second set of data. The at least one processor may generate a CT image of the object based on the third set of data.

Another aspect of the present disclosure relates to a non-transitory computer readable medium for air calibration. The non-transitory computer readable medium storing executable instructions that when executed by at least one processor, cause the at least one processor to effectuate a method. The method may include one or more following operations. A first set of data associated with air in a scanning area may be obtained. A second set of data associated with an object in the scanning area may be obtained. The second set of data based on the first set of data may be calibrated, and a set of reference values generated by a neural network model may be used to perform the calibration. A third set of data based on the calibration of the second set of data may be generated. Based on the third set of data, a CT image of the object may be generated.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A and FIG. 1-B are schematic diagrams illustrating an exemplary CT system according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
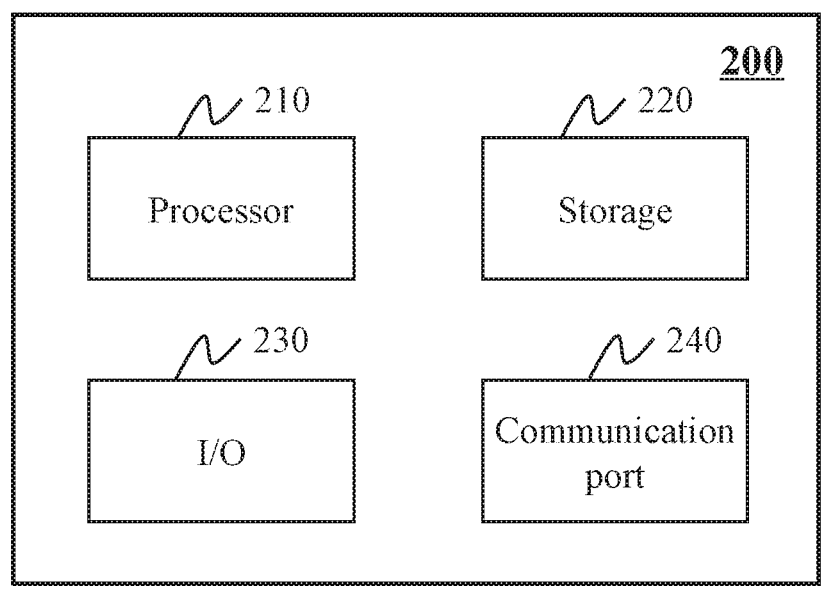
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/black may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, an emission computed tomography (ECT) system, a magnetic resonance imaging (MRI) system, an ultrasonography system, a positron emission tomography (PET) system, or the like, or any combination thereof.

The method and system disclosed herein may be used to perform an automatic and self-improving correction when scanning an object. The correction may be based on a neural network. In some embodiments, the correction may be based on a neural network of deep learning type. For example, the correction may be based on a deep believe network (DBN). Compared with existing technology, the method disclosure herein may be more accurate and fast. The method disclosed herein is scalable in handling large amount of CT raw data, while maintaining efficiency of data processing. The modeling within the neural network may be personalized or categorical. In other words, the modeling within the neural network may incorporate personal information relating to an object, thus rendering the correction tailored to the personal characteristics. In some other embodiments, the modeling within the neural network may focus on the common features within a group of objects, thus rendering the correction tailored to the categorical characteristic of the group. Further, the computation time may be reduced significantly after the neural network has been trained.

The method and system disclosure herein may be applied for reconstruction of other types of images including, for example, CT images, ECT images, magnetic resonance (MR) images, PET images, etc. For illustration purposes and not intended to limit the scope of the present disclosure, the disclosure is provided in connection with CT image reconstruction. The system may reconstruct a CT image based on a statistical image reconstruction algorithm. The statistical image reconstruction algorithm may include a regularization item that may be used to reduce staircase artifacts during the statistical image reconstruction.

The following description is provided to help better understanding CT image reconstruction methods and/or systems. The term "image" used in this disclosure may refer to a 2D image, a 3D image, a 4D image, and/or any related image data e.g., CT data, projection data corresponding to the CT data). This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

FIGS. 1-A and 1-B are schematic diagrams illustrating an exemplary CT system according to some embodiments of the present disclosure. As shown in FIG. 1-A, the CT system 100 may include a CT scanner 110, a network 120, one or more terminals 130, a processing engine 140, and a storage device 150.

The CT scanner 110 may include a gantry 111, a detector 112, a detecting region 113, a table 114, and a radioactive scanning source 115. The gantry 111 may support the detector 112 and the radioactive scanning source 115. A subject may be placed on the table 114 for scanning. The radioactive scanning source 115 may emit radioactive rays to the subject. The detector 112 may detect radiation events (e.g., gamma photons) emitted from the detecting region 113. In some embodiments, the detector 112 may include one or more detector units. The detector units may include a scintillation detector (e.g., a cesium iodide detector), a gas detector, etc. The detector unit may be and/or include a single-row detector and/or a multi-rows detector.

The network 120 may include any suitable network that can facilitate exchange of information and/or data for the CT system 100. In some embodiments, one or more components of the CT system 100 (e.g., the CT scanner 110, the terminal 130, the processing engine 140, the storage device 150, etc.) rrray communicate information and/or data with one or more other components of the CT system 100 via the network 120. For example, the processing engine 140 may obtain image data from the CT scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the CT scanner 110, the terminal 130, and/or the storage device 150. For example, the processing engine 140 may process image data and determine a regularization item that may be used to modify the image data. In some embodiments, the processing engine 140 may be a single server or a server group. The server group may be centralized or distributed. In some embodiments, the processing engine 140 may be local or remote. For example, the processing engine 140 may access information and/or data stored in the CT scanner 110, the terminal 130, and/or the storage device 150 via the network 120. As another example, the processing engine 140 may be directly connected to the CT scanner 110, the terminal 130 and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any core combination thereof. Exemplary mass storage may include a magnetic disk, an optical disk, a solid-state chive, etc, Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable RUM (EPROM), an electrically erasable programmable ROM (EEPROM), a compact disk ROM (CD-ROM), and a digital versatile disk RUM, etc. in some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the CT system 100 (e.g., the processing engine 140, the terminal 130, etc.). One or more components in the CT system 100 may access the data or instructions stored in the storage device 150 via the network 120. In some embodiments, the storage 150 may be directly connected to or communicate with one or more other components in the CT system 100 (e.g., the processing engine 140, the terminal 130, etc). In some embodiments, the storage device 150 may be part of the processing engine 140. The connection between the components in the CT system 100 may be variable. Merely by way of example, as illustrated in FIG. 1-A, the CT scanner 110 may be connected to the processing engine 140 through the network 120. As another example, as illustrated in FIG. 1-B, the CT scanner 110 may be connected to the processing engine 140 directly.

FIG. 2 is a schematic diagram illustrating exemplary hardware and/or software components of an exemplary computing device according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the CT scanner 110, the terminal 130, the storage device 150, and/or any other component of the CT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the CT scanner 110, the terminal 130, the storage device 150, and/or any other component of the CT system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the CT scanner 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a Wiviax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
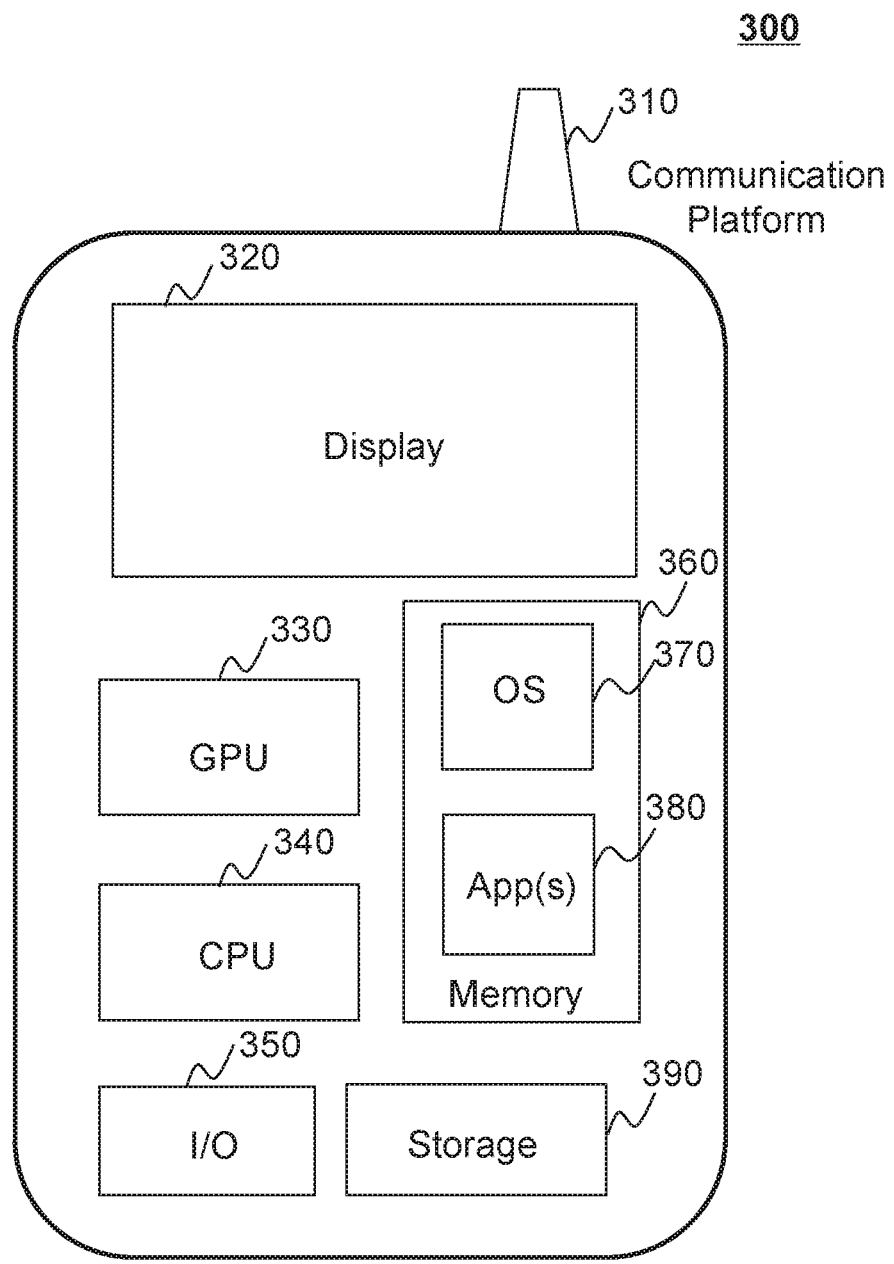
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the CT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
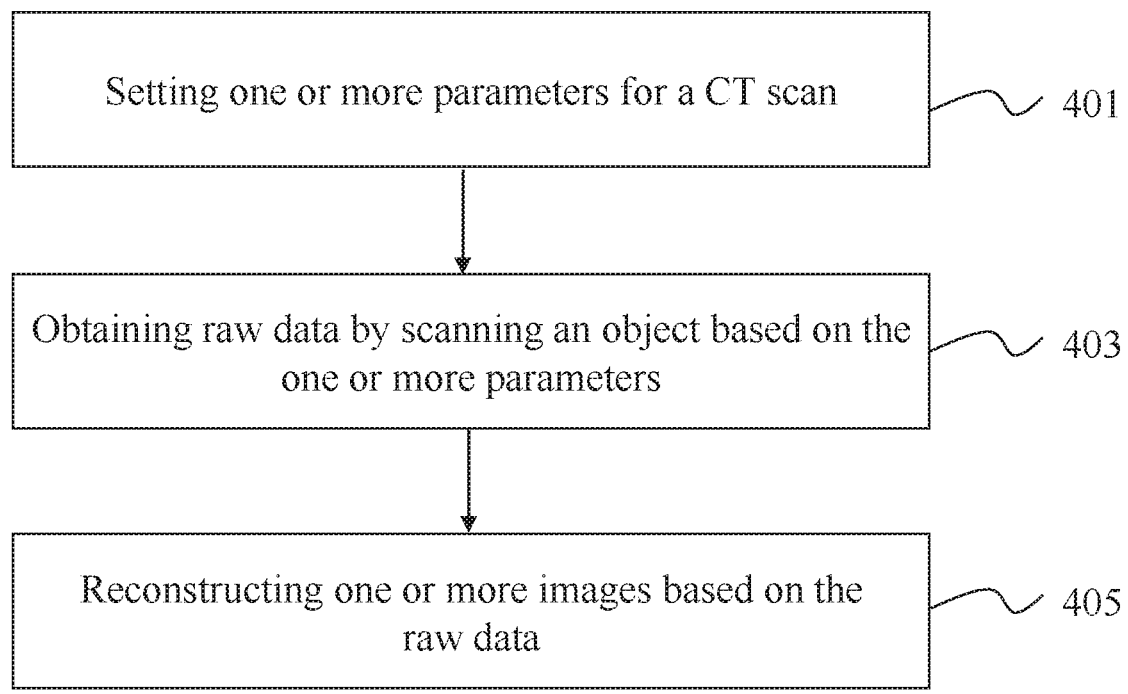
FIG. 4 is a flowchart illustrating an exemplary image generating process according to some embodiments of the present disclosure.

FIG. 4 is a flowchart illustrating an exemplary image generating process according to some embodiments of the present disclosure. The flowchart 400 may be implemented as a set of instructions in a non-transitory storage medium of the processing engine 140 and/or the terminal 130 of the system 100. The processing engine 140 and/or the terminal 130 may execute the set of instructions and may accordingly perform the steps in the flowchart 400.

In 401, the processing engine 140 and/or the terminal 130 may set one or more parameters for a scan are. The parameters may be determined by scanning protocols. In some embodiments of the present disclosure, the scanning protocols may be generated for scanning different objects. Merely by way of example, the scanning protocols may be with respect to a collimator aperture, a detector aperture, an X-ray tube voltage and/or current, a scan mode, a table index speed, a gantry speed, a reconstruction field of view (FOV), kernel, or the like, or any combination thereof. In some embodiments, the scan mode may further include a scanning time interval, a target location information, the position of the gantry, or the like. By way of example, the table 114 may be rotated to a location. As yet another example, the gantry 111 may be moved to a location. In some embodiments, the locations may be set by a user (e.g., a doctor, a nurse). The positions may be different depending on the object to be scanned.

In step 403, raw data may be obtained by scanning an object based on the one or more parameters. Merely by way of example, the object may include a substance, a tissue, an organ, a specimen, a body, or the like, or any combination thereof. In some embodiments, the object may include a patient or a part thereof. The objet may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. The raw data may include the intensity of the X-rays. As an example, the raw data may be received by the detectors through X-ray attenuation through object.

In 405, one or more images based on the raw data may be reconstructed. In some embodiments, 405 may be implemented by image processing engine 140. The reconstruction images may include an MRI image, a CT image, a PET image, or any combination of the above-described images. In other embodiments, the reconstruction images may include a two-dimensional (2D) image or a three-dimensional (3D) image. In some embodiments, the reconstruction process may include filtering denoising of the image, air correction, slice normalized correction, or the like. The reconstruction may be performed using a plurality of algorithm. Merely by way of example, the reconstruction of the images may be based on methods including Fourier slice theorem, filtered back projection algorithm, fan-beam reconstruction, iterative reconstruction, etc.

It should be noted that the flowchart described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure.

Figure 5:
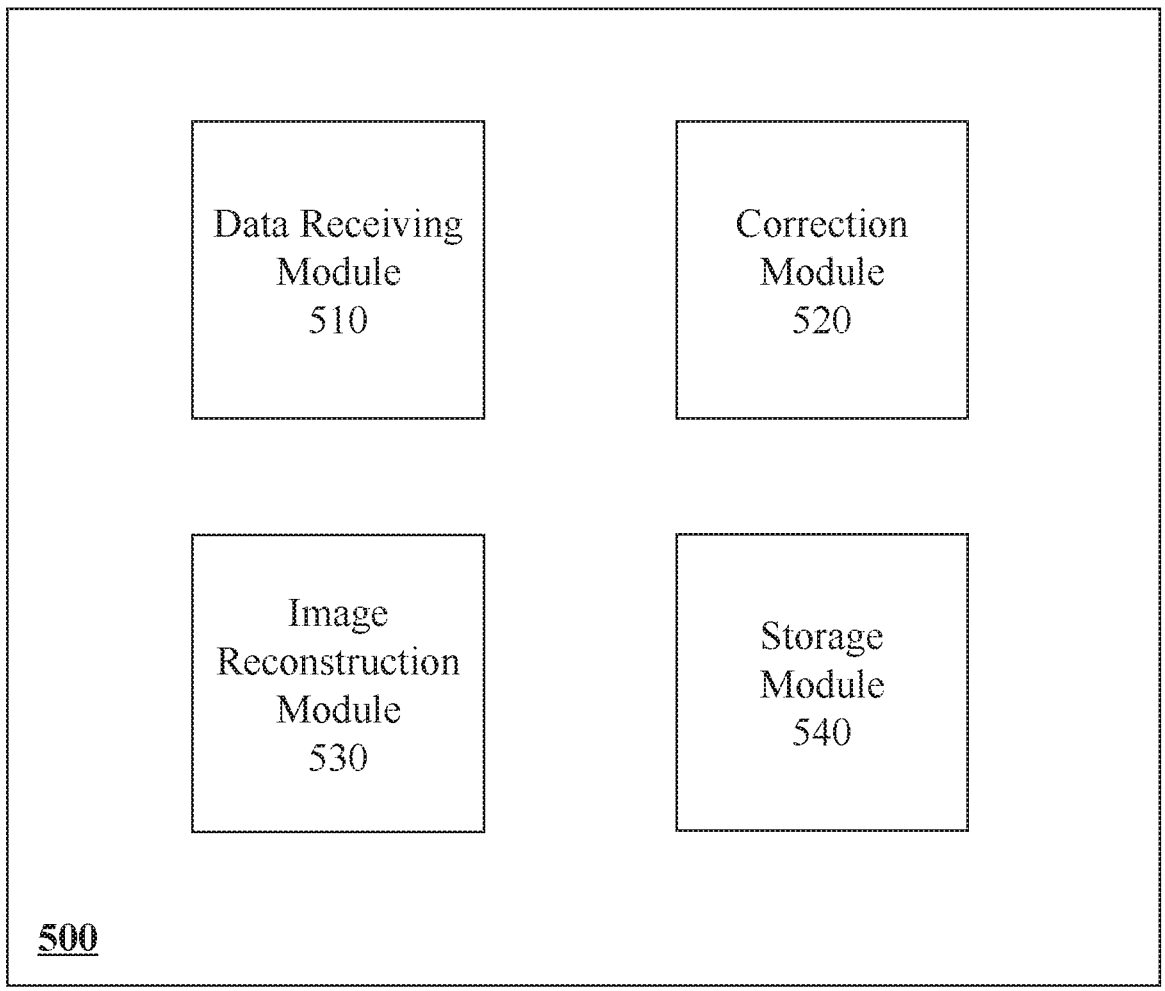
FIG. 5 is a block diagram illustrating an exemplary correction engine according to some embodiments of the present disclosure.

FIG. 5 is a block diagram illustrating an exemplary correction engine according to some embodiments of the present disclosure. In some embodiments, the correction engine 500 may be implemented on the processing engine 140 and/or the terminal 130. The correction engine 500 may include a data receiving module 510, a calibration module 520, an image reconstruction module 530, and a storage module 540.

The data receiving module 510 may be configured to acquire data related to a scan process (for example, a scan process in which an object is scanned) and/or data related to the imaging system. The data related to a scan process may include general information of the object, such as age, height and weight, gender, medical history, or the like, or any combination thereof. In some embodiments, the data related to the imaging system may include scanning protocol, raw data, detector temperature, correction parameters, X-ray intensity, or the like, or any combination thereof. In some embodiment, the data receiving module 510 may acquire data from the detector 112, such as the detector temperature. In some embodiments, an operator (e.g., a doctor, a nurse) may set a temperature measurement device (not shown) at the terminal 130 to acquire the detector temperature, and transmit the detector temperature from the terminal 130 to the data receiving module 510. In some embodiments, the radioactive scanning source 115 may emit the X-rays to the subject. The X-rays may pass through the subject and may attenuate during the passing process. The attenuated X-rays may be detected by the detector 112 and transmitted to the data receiving module 510. In some embodiments, the acquired data may be transmitted to the storage module 540 to be stored. In some embodiments, the data acquired by the data receiving module 510 may be transmitted to the image reconstruction module 530 to construct the image, and may be further transmitted the image calibration module 520 to correct the data. For example, the data receiving module 510 may transmit the receiving correction parameters to the image calibration module 520 for artifact correction and/or update a correction table.

The calibration module 520 may be configured to perform a correction during the process of image reconstruction. In some embodiments, the correction may include gas correction (air correction), center correction, water correction, slice normalization correction, or the like, or any combination thereof. Air correction and water correction may produce a pre-scanned data in the air or water based on the scan (for example, a CT scan) of slices in the air or water. Thereafter, the pre-scanned data may be subtracted from the scanned data of the object in a subsequent scan to obtain corrected scanned data of the object. Center correction or other types of system correction may also be used to monitor the locations or the Cartesian coordinate of the X-ray tube. Slice normalization correction may be performed on the basis of the air correction. Merely by way of example, the air correction may not correct the artifact caused by the difference between every slice of the detectors. Thereafter, the data corrected by the slice normalization correction together with the air correction data may be subtracted from the scanned data of the object in a subsequent scan. In some embodiments, the calibration module 520 may obtain raw data from the data receiving module 510 and the storage module 540 and calibrate the raw data. In other embodiments, the calibration module 520 may perform an air scanning. The air scanning is performed without object on the gantry 114 in the image system 100. For example, the calibration module 520 may generate an air correction table by the air scanning. The air correction table may include one or more air correction parameters. In some embodiments, the air correction table may be updated based on a plurality of reference values. The reference values may be generated by a neural network. The reference value may be the same data type as the one or more air correction parameters in the correction table. Additionally or alternatively, the air correction table may be stored in the storage module 540. In some embodiments, the calibration module 520 may transmit data to image reconstruction module 530 to reconstruct the image.

The image reconstruction module 530 may be configured to reconstruct CT images of a scanned object in some embodiments, the image reconstruction module 530 may reconstruct the images from the raw data obtained from the data receiving module 510 and/or the corrected data from the calibration module 520. In some embodiments, the image reconstruction module 530 may generate images according to the data from the storage module 540. In some embodiments, the image reconstruction module 530 may process the reconstructed images. The processing may include smoothing, gray scale normalization, and the like, and any combination thereof. For example, during an image reconstruction process, a surface of a tissue in an image may be smoothed. In some embodiments, the image reconstruction module 530 may reconstruct images according to reconstruction parameters. The reconstruction parameters may include reconstruction field of view, reconstruction matrix, convolution kernel/reconstruction filter, or the like, or any combination thereof. Merely by way of example, the reconstruction of the images may be based on methods utilizing the Fourier slice theorem, the filtered back projection algorithm, the fan-beam reconstruction, and/or the iterative reconstruction, etc.

The storage module 540 may be configured or used to store information received from the data receiving module 510, the calibration module 520, and/or the image reconstruction module 530. The information may include scanning protocols, scanning parameters, raw data, neural network, air correction table, air correction parameters, slice normalization correction table, reconstructed images, reference values, or the like, or a combination thereof. In some embodiments, the storage module 540 may store one or more programs and/or instructions that may be executed by processor(s) of the processing engine 140 to perform exemplary methods described in this disclosure. For example, the storage module 530 may store program(s) and/or instruction(s) that can be executed by the processor(s) of the processing engine 140 to acquire raw data, reconstruct a CT image based on the raw data, and/or display any intermediate result or a resultant image. In some embodiments, the storage module 540 may include one or more components, including a hard disk driver, a magnetic tape, a removable storage drive (e.g., a phase change rewritable optical disk drive, a magneto-optical drive, a USB removable hard disk, etc.), a microdrive, or the like, or a combination thereof.

It should be noted that the above description of the processing module is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more units in the correction module 530 may include a correction table generating unit (not shown) respectively. As another example, any two or more units may be combined as an independent unit used to implement more than one functions. As a further example, the function of the storage module 540 may be implemented on the data receiving module 510 or the image reconstruction module 530, or the combination thereof. As still a further example, any one of the units may be divided into two or more sub-units.

Figure 6:
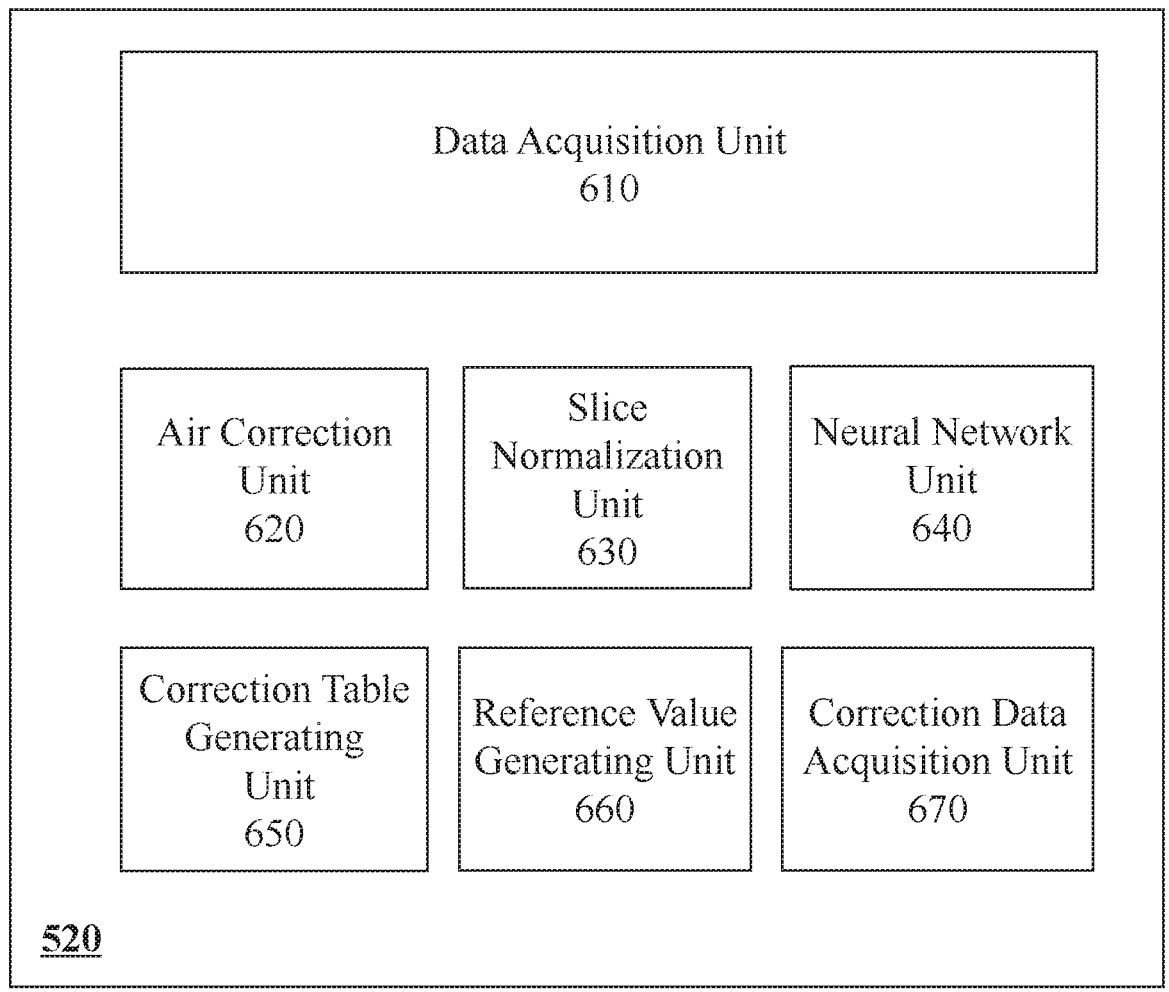
FIG. 6 is a block diagram illustrating an exemplary correction module according to some embodiments of the present disclosure.

FIG. 6 is a block diagram illustrating an exemplary correction module according to some embodiments of the present disclosure. The correction module 520 may include a data acquisition 610, an air correction unit 620, a slice normalization correction unit 630, and a neural network unit 640, a correction table unit 650, a reference value generating unit 660, and a correction data acquisition unit 670.

The data acquisition unit 610 may be configured to acquire data related to the imaging system. The data may include scanning data, scanning protocol, image data, raw data, detector temperature, correction parameters, X-ray intensity, or the like, or any combination thereof. In some embodiments, the data acquisition 610 may acquire data from data receiving module 510, the image reconstruction module 530, and/or storage module 540. In some embodiments, the data acquisition 610 may acquire data from any external device (e.g. database, terminals) related to the imaging system 100. In some embodiments, the data acquisition unit 610 may acquire data from users (e.g. doctor, patient).

The air correction unit 620 may be configured to perform an air correction. The air correction may be performed based on different types of data. The different types of data may include air scanning data, raw data, scanning data, reference values, and air correction table. The air scanning data may be obtained by scanning air in a scanning area. In some embodiments, the air scanning may be performed without any object on the gantry 114 in the imaging system 100. In some embodiments, the reference values may include X-ray intensity values. Merdy as an example, the reference values may be generated in the reference detectors of the imaging system 100 and used for performing an air calibration in the reconstruction of an image. In some embodiments, the reference values may be generated by a neural network. In some embodiments, the air correction table may be obtained under different scanning protocols. The air correction table may be affected by a plurality of factors. The factors may include inter-detector gain, system operation condition, season, ambient temperature. For instance, the air correction table may be changed if the temperature of the detectors changed during working. In some embodiments, the air correction may require a period of time that lasts front a few minutes to more than half-hour to be completed and is often performed only once a day before scanning a patient. The air correction unit 620 may perform an air correction on the basis of data from the data acquisition unit 610 and the neural network unit 640.

The slice normalization correction unit 630 may be configured to perform a slice normalization correction for image reconstruction. In some embodiments, the slice normalization correction is a supplement correction for the air correction. As an example, the slice normalization correction may be performed if the air correction could not distinguish the difference between every slice of the detectors. The gain of every slice of the detectors may be different, and this may cause artifacts in the air correction. The artifacts may include ring artifacts, strip artifacts, etc. The slice normalization correction may also be performed based on the reference values generated by reference detectors. In some embodiments, the reference detectors in the imaging system may include a detector array. The detector array has a plurality of substantially contiguous rows of detectors and the fan beam of the imaging system is made sufficiently "thick" to illuminate all the rows of detectors. The detector array may be configured to measure the flux, spatial distribution, spectrum, and/or other properties of X-rays, or the like, or any combination thereof. In some embodiments, the reference detectors located on both sides of the detectors. The reference values may be generated by a neural network from the neural network unit 640. The slice normalization correction unit 620 may perform an air correction on the basis of data from the data acquisition unit 610, the air correction unit 630 and the neural network unit 640.

The neural network unit 640 may be configured to generate the reference values for the air correction and the slice normalization correction. The reference values may be associated with air scanning data, scanning data, air correction table, slice normalization correction table, intensity of the X-ray, scanning protocol, temperature, or the like, or any combination thereof. In some embodiments, the neural network unit 640 may include a plurality of neural networks. The neural network may be trained with a general set of data to function as a general model of a machine or process with an input set. The neural network may be tested/trained with a set of training data. The neural network may be determined according to different fields and problems. The neural network may include artificial neural network. In some embodiments, the artificial neural network may include neural network model such as Long short term memory (LSTM) neural network, Deep believe network (DBN), Generative adversary network (GAN), Gradient boosting decision tree (GBDT), Back Propagation, Hopfield, Kohonen, Perceptron, Elmman, Jordan, or the like, or any combination thereof. The neural network unit 640 may include a deep learning neural network model. In some embodiments, the learning method may include unsupervised learning and supervised learning.

The correction table generating unit 650 may be configured to acquire a correction table. The correction table may include an air correction table and/or a slice normalization correction table. The correction table may include one or more parameters. The one or more parameters may include the intensity of the X-ray. The one or more parameters may be generated by a reference detector (e.g. an edge detector). In some embodiments, the edge detector may be positioned on two sides of detectors. The intensity of the X-ray may be obtained at each angle by the edge detector. In some embodiments, the correction table may be generated based on the reference detector. Additionally or alternatively, the correction table may be stored in the storage module 540. In some embodiments, the correction table generating unit 650 may transmit data to the image reconstruction module 530 to reconstruct the image. The reference value generating unit 660 may be configured to obtain the reference values for a correction. The correction may be performed using the reference values generated from the neural network unit 640. The correction data acquisition unit 670 may receive data from the correction table generating unit 650 and the reference value generating unit 660.

It should be noted that the above description of the processing module is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the slice normalization correction unit 630 may be integrated into the air correction unit 620. As another example, any two or more units may be combined as an independent unit used to implement more than one functions. As a further example, the neural network unit 540 may be necessary and integrated into respect in both the air correction unit 620 and the slice normalization correction unit 630. As still a further example, any one of the units may be divided into two or more sub-units.

Figure 7:
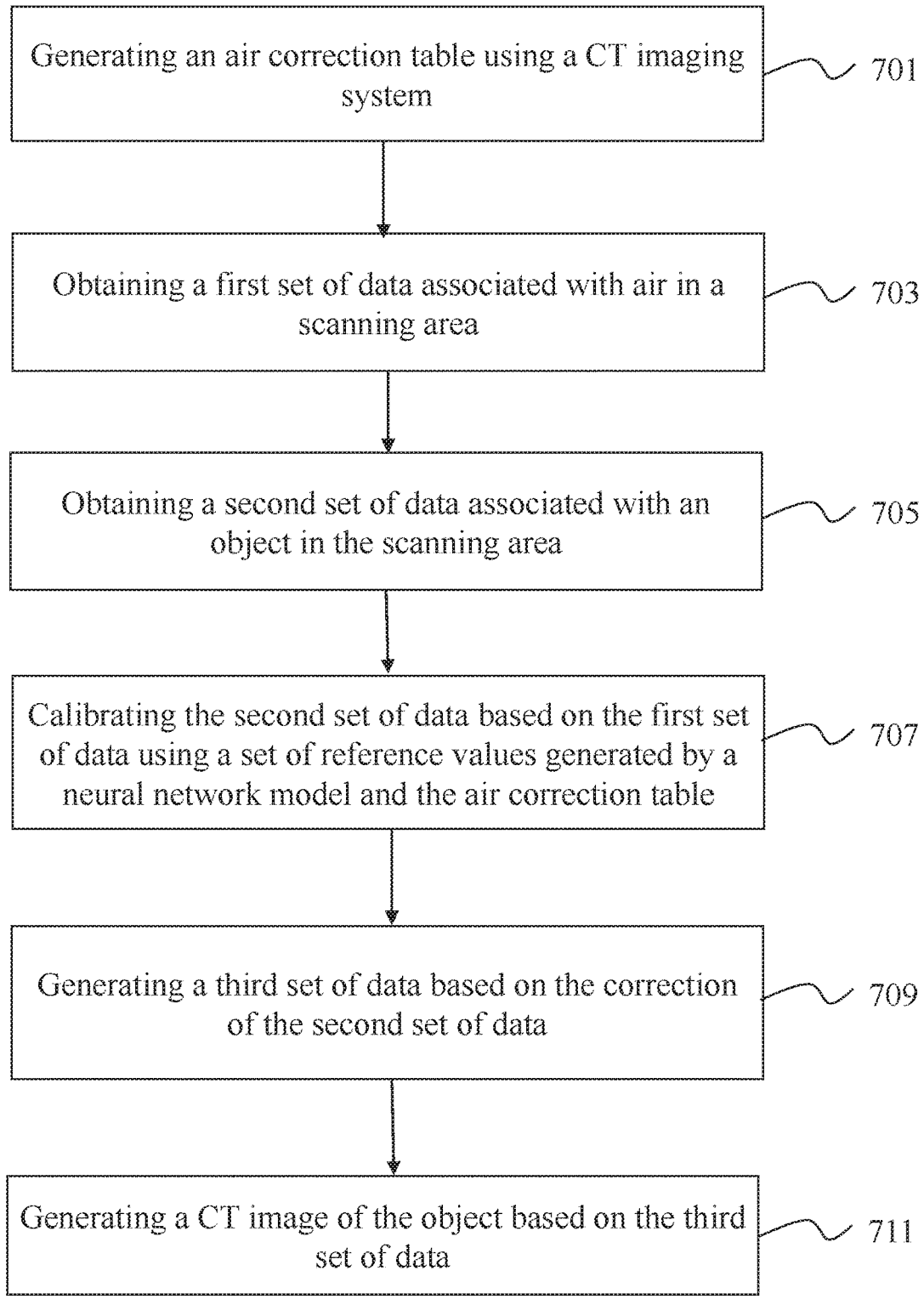
FIG. 7 is a flowchart illustrating an exemplary process for air correction according to some embodiments of the present disclosure.

FIG. 7 is a flowchart illustrating an exemplary process for air correction according to some embodiments of the present disclosure. In some embodiments, at least part of process 700 may be performed by or be implemented on one or more components of the X-ray imaging system 100 as shown in FIG. 1.

In 701, an air correction table may be generated using a CT imaging system. In some embodiments, the air correction table may be generated by the correction table generating unit 650. The air correction table may be generated under a scanning protocol. The scanning protocol may include a plurality of parameters. Merely by way of example, the parameters may be with respect to a collimator aperture, a detector aperture, an X-ray tube voltage and/or current, a scan mode, a table index speed, a gantry speed, a reconstruction field of view (FOV), kernel, or the like, or any combination thereof. In some embodiments, the air correction table is generated by performing an air scanning, i.e. no object in the gantry for scanning. During a scanning procedure of the patient, the detectors are exposed to one or more X-rays from the X-ray source and generate signals responsive to the one or more X-rays when only air is located between the X-ray source and the detectors. In some embodiments, the air correction table is generated for eliminating the inter-detector gain inconsistency. The inter-detector gain inconsistency is affected by a plurality of factors of the detectors. The factors may include size of the pixel unit, surface flatness, the reflection between the pixel units, photoelectric conversion device response, and noise of the data acquisition of electronic system. In other embodiments, the inter-detector gain may change with time and temperature. The changes may include temperature changes, radiation damage, changes in communication links that transmit data from the detectors mounted on the gantry rotor to the gantry's stator. The inter-detector gain inconsistency may produce ring artifacts during image reconstruction. In some embodiments, the air correction table is generate under a pre-set temperature and a pre-set scanning protocol. The air correction table may be different under different temperature and different scanning protocol. The air correction table may be updated regularly in a period of time or randomly. In some embodiments, the air correction table include air correction parameters, such as the return value of the detectors, the intensity of the X-ray, etc.

In 703, a first set of data associated with air in a scanning area may be obtained. In some embodiments, the first set of data may be obtained by the air correction unit 620. The first set of data may be generated in an air scanning. The air scanning is performed without object on the gantry. The first set of data may include the return value of the detectors, the intensity of the X-ray, etc. In some embodiments, the first set of data may be related to the air correction table and/or the raw data.

In 705, a second set of data associated with an object in a scanning area may be obtained. In some embodiments, the second set of data may be obtained by the air correction unit 620. The second set of data may be generated in a CT scanning under the same scanning protocol as the air scanning. The CT scanning is performed with an object on the gantry. In other embodiments, the object may include a substance, a tissue, an organ, a specimen, a body, or the like, or any combination thereof. In some embodiments, the object may include a patient or a part thereof. The object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. The second set of data may include the return value of the detectors across the object, the intensity of the X-ray across the object.

In 707, the second set of data is calibrated based on the first set of data using a set of reference values generated by a neural network model and the air correction table. The calibration may be performed by the reference value generating unit 660. In some embodiments, the calibrating may be implemented by an algorithm as an example shown below:

$$(\mu D)_{obj} = (A_{DTC\_obj} - A_{ALT\_obj}) - (A_{DTC\_air} - A_{ATL\_air}) \qquad (1)$$

$$A_{ALT} = f(A_{DTC\_obj}, A_{DTC\_air}, mA, \ldots) \qquad (2)$$

wherein $A_{DTC\text{-}obj}$ is the return value of the detectors across the object, $A_{DTC\text{-}air}$ is the air correction table, $A_{ALT\text{-}air}$ is reference value that represents the return value of the detectors across the air, $A_{ALT\text{-}obj}$ is reference value that represents the return value of the detectors across the object, mA is the milli-ampere value of the X-ray tube current, f is a deep learning neural network where the output of f $A_{ALT}$, is the estimated value to mimic the reference value given by each row of detectors under each view.

In some embodiments, the calibrating may be implemented by an algorithm as an example:

$$A_{ALT}(:,j) = f(A_{DTC\text{-}obj}(:,j-p:j+q), A_{DTC\text{-}air}, mA(j-p:j+q), \ldots) \qquad (3)$$

wherein j is the index indicating the $j^{th}$ view of the detectors, $A_{DTC\_obj}(:,j-p:j+q)$ contains the raw data from the p view detectors before the $j^{th}$ view detectors to the q view detectors after the $j^{th}$ view detectors across the object, $A_{DTC\text{-}air}$ the air correction table, mA(j−p:j+q) indicates the milli-ampere value of the X-ray tube current from the p view detectors before the $j^{th}$ view detectors to the q view detectors after the $j^{th}$ view detectors, $A_{ALT}(:,j)$ is the alternate reference value that represents the return value of the $j^{th}$ view detectors, f is a deep learning neural network.

In some embodiments, the neural network may include at least three types of layers (e.g. one or more input layers, one or more hidden layers, and one or more output layers). The input layers may be configured to input data. The data may include the return value of the detectors $A_{DTC\text{-}obj}$, the air correction table $A_{DTC\text{-}air}$, the intensity of the X-ray and/or other scanning data. The hidden layers may be configured to process the data from the input layers. The output layers may be configured to output the processed data from the hidden layers. The output data may include reference values (e.g. $A_{ALT\text{-}obj}$, $A_{ALT\text{-}air}$). The neural network may include a deep learning neural network model. The deep learning neural network model may be trained using a plurality of training data associated with at least one detector of the CT imaging system. The plurality of training data includes a set of data covering the return values of desired reference detectors under each of the scan protocol required. In some embodiments, the plurality of training data may be obtained through experiments and/or computational simulation. Simulation of the return values of desired reference detectors fluctuation may be added into the plurality of training data to form a new set of data. The new set of data may be a new training data for the neural network. The goal of the deep learning neural network is to minimize the value of the $\min\|\{y_i\} - \{y_i\}_0\|$, wherein $\{y_i\}_0$ are the return values of desired reference detectors and $\{y_i\}$ are the output values of the neural network which represent the reference values.

In 709, a third set of data based on the correction of the second set of data is generated. In some embodiments, the third set of data may be generated by the correction data acquisition unit 670. The first set of data associated with air in a scanning area may be subtracted from the second set of data associated with an object in the scanning area to obtain the third set of data (e.g. $(\mu D)_{obj}$).

In 711, a CT image of the object based on the third set of the data is generated. The object may be a human body (for example, a patient), a part of the human body, an X-ray-safe item whose inner structure needed to be imaged non-invasively or on-destructively (e.g., an antique, an instrument, etc.), or the like. Merely by way of example, the second set of data may be generated by a CT scan or it may be obtained from other resources (e.g., a computer-simulated scan). In some embodiments, the CT image is generated according to a reconstruction algorithm may generate a CT image relating to the object obtained from a transformation of the third set of data. Examples of such reconstruction algorithms may include those based on Feldkamp-Davis-Kress (FDK) reconstruction, maximum a posteriori probability (MAP), maximum likelihood (ML), algebraic reconstruction technique (ART), entropy-based optimization, least squares (LS) or penalized weighted least squares (PWLS), or the like, or a combination thereof. The described algorithms may be executed once, or may be executed iteratively. Additionally, the third set of data acquired may proceed to noise estimation. A noise model may be acquired by noise estimation. The noise estimation may include estimating the noise contained in the third set of data by fitting one or more noise models to the estimated noise. As used herein, the noise may include electronic noises that may be generated by an electronic device, e.g., a sensor, the circuitry of the scanner, or the like, or a combination thereof. The noise model(s) may indicate the noise distribution of an image, noise amplitude at respective point(s) of an image, or the like, or a combination thereof. The generation of the CT image described may include an iterative reconstruction process that may include a computer based iterative processing. The above mentioned examples of models are provided for illustration purposes and not intended to limit the scope of the present disclosure. Exemplary reconstruction parameters may be the slice thickness, parameters relating to the voxel model (for example, a rectangular voxel model, a cubic voxel model, a spherical voxel model, etc. or the like, or a combination thereof. As used herein, reconstruction parameters may be set by the users based on different conditions. In some embodiments, the noise variance may be reduced. The method for reducing the noise variation may include obtaining the second set of data by scanning an object, calibrating the second set of data by air calibration to obtain the third set of data, generating a calibrated noise variance based on the third set of data, and reducing the calibrated noise variance to produce a reduced noise variance.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, step 701 may be unnecessary and the third set of data may be generated based on more data.

Figure 8:
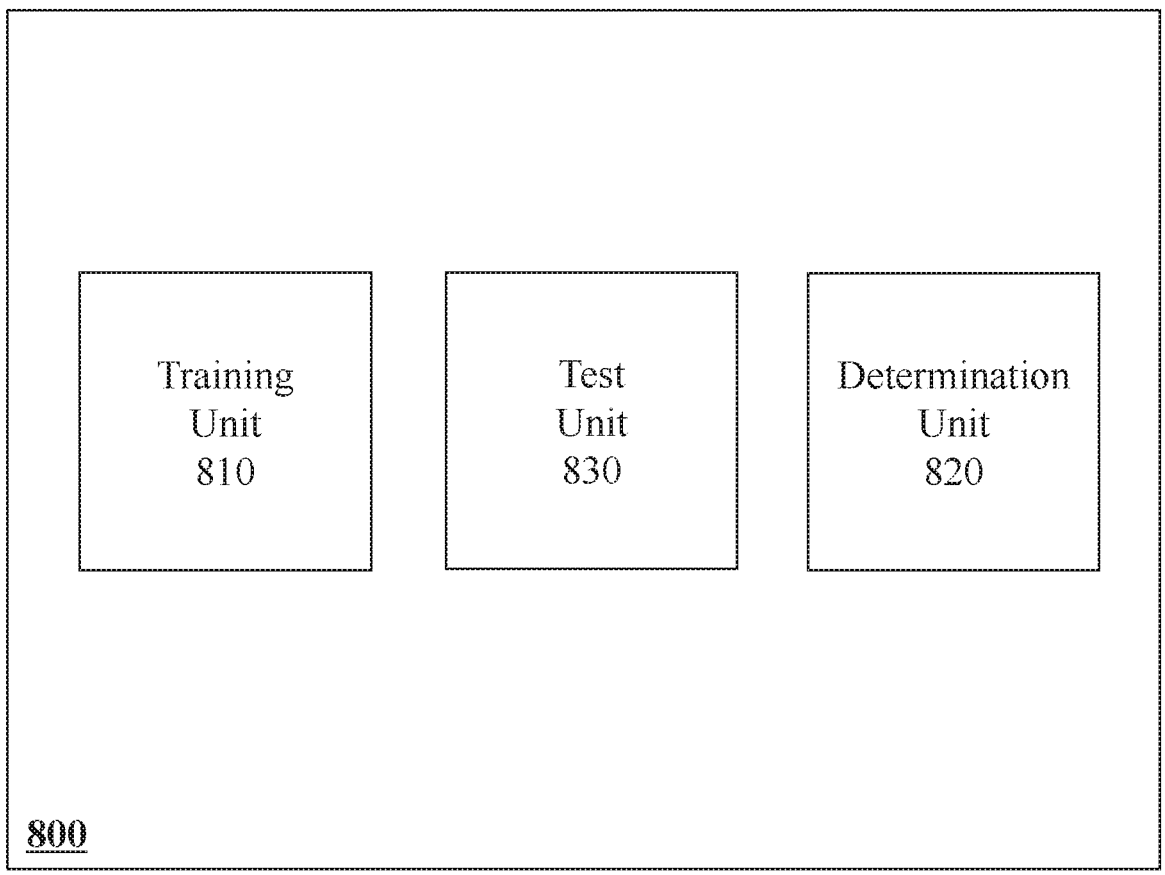
FIG. 8 is a block diagram illustrating an exemplary neural network according to some embodiments of the present disclosure.

FIG. 8 is a block diagram illustrating an exemplary neural network according to some embodiments of the present disclosure. The neural network may be implemented on the processing engine 140 and/or terminal 130. The neural network may include a training unit 810, a testing unit 820, and a determination unit 830. The training unit 810 may be configured to obtain a set of training data. The testing unit 820 may be configured to test the neural network trained by the training unit 810. The determination unit 830 may be configured to determine an appropriate neural network according to different technical fields and problems to be solved.

Figure 9:
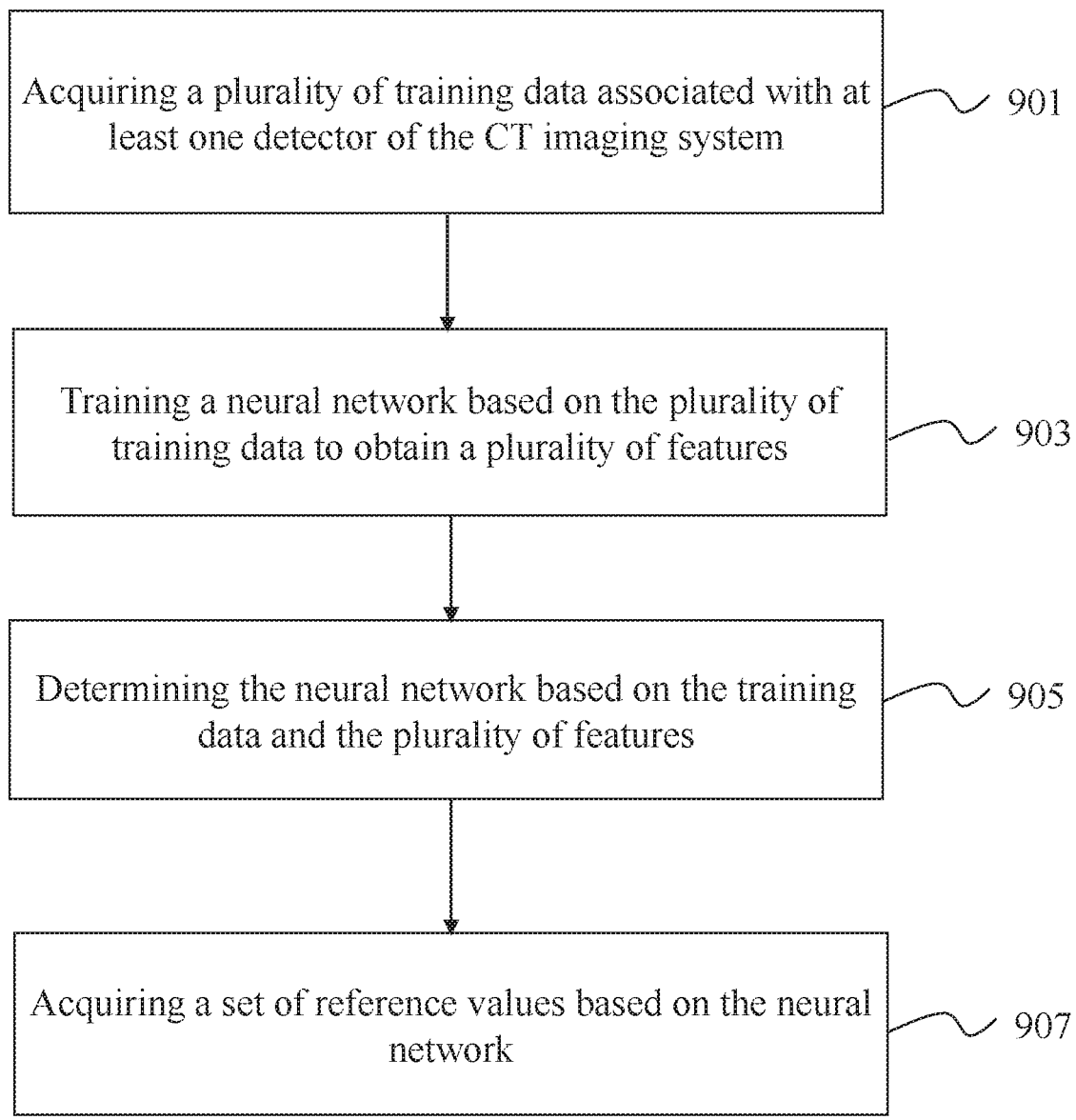
FIG. 9 is a flowchart illustrating an exemplary process for acquiring a reference values based on the neural network according to some embodiments of the present disclosure.

FIG. 9 is a flowchart illustrating an exemplary process for acquiring a reference values based on the neural network according to some embodiments of the present disclosure.

In 901, a plurality of training data associated with at least one detector of the CT imaging system is acquired. The plurality of training data may be acquired by the training unit 810. The plurality of training data includes a set of data covering the return values of desired reference detectors of each of the scanning protocol required. In some embodiments, the plurality of training data may be obtained through experiments and/or computational simulation. Simulation of the return values of desired reference detectors fluctuation may be added into the plurality of training data to form a new set of data. The fluctuation may include a parameter, a function, etc. In some embodiments, the training data may be pre-processed according to various algorithms. The pre-processing may include noise reduction, dimensionality reduction, sample selection, or the like, or any combination thereof. The algorithms may include factor analysis, clustering analysis, etc.

In 903, a neural network is trained based on the training data and the plurality of features. The neural network is trained by the training unit 810 and the testing unit 820. The neural network based on the training data may work as a general model. The plurality of features may be defined according to technical fields and/or problems to be solved. The neural network may have properties of nonlinearity, non-convexity, non-locality, non-stationary, adaptivity, fault tolerance, or the like, or the combination of thereof. In some embodiments, training the neural network may be related to a plurality of algorithm and parameters. The algorithm may include non-linear calculation, integral transformation, gradient calculation, iteration, etc. The parameters may include error function, weighting coefficient, rate of convergence, etc.

In 905, the neural network may be determined based on the training data and the plurality of features. The neural network may be determined by the determination unit 830. In some embodiments, the neural network may be determined when the number of iterations reaches a threshold according to the algorithm. A plurality of testing data is required for verifying the neural network. The plurality of testing data is used for assessing the performance of the neural network. In some embodiments, the testing data includes an input and an expected output which is obtained from a plurality of experimental data. The actual output of the neural network may be compared with the expected output. The difference between the outputs may be in a range. The neural network may be determined when the error function associated with the expected output and the actual output varies in a pre-determined range.

In 907, a set of reference values based on the neural network is acquired. The neutral network works as a general model of a process with an input. The set of reference values may be determined by determination unit 830. The input may include the return values of desired reference detectors, $A_{DTC\text{-}obj}$, the air correction table $A_{DTC\text{-}air}$, the intensity of the X-ray and/or other scanning data. The output of the neural network may be a set of reference values. The reference values may be the same data type with the air correction table.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure example, 903 and 905 may be put in one step.

Figure 10:
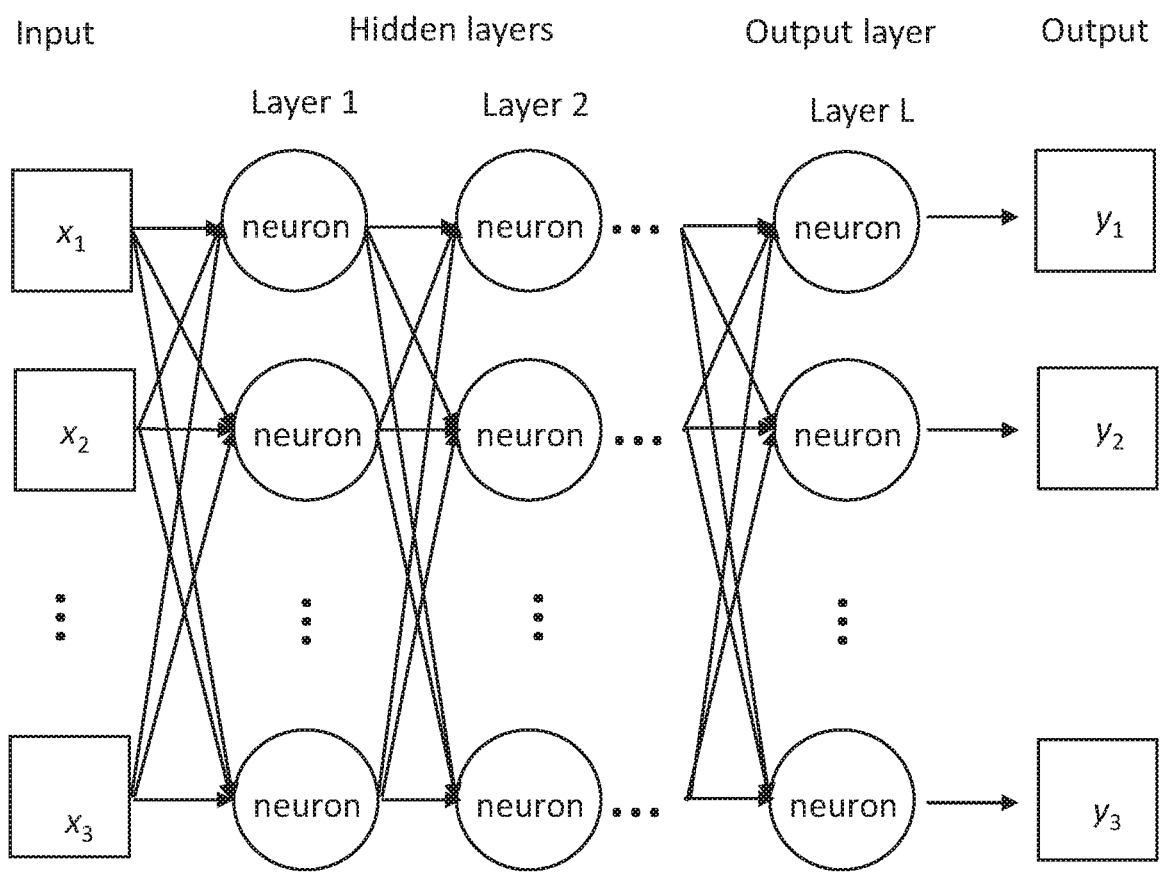
FIG. 10 is a flowchart illustrating an exemplary graphical representation of a neural network according to some embodiments of the present disclosure.

FIG. 10 is a flowchart illustrating an exemplary graphical representation of a neural network according to some embodiments of the present disclosure. A neural network according to the present disclosure includes a plurality of neurons connected therein. As shown in FIG. 10, according to their functions, the plurality of neurons of the neural network can be divided into three different types of groups (i.e., layers). The first type of layer may be an input layer for receiving a set of data representing the input pattern, the second type of layer may be an output layer for providing a set of data representing the output pattern, and the third type of layer having an arbitrary number of neurons may be a hidden layer, which converts the input pattern into an output pattern. Since the number of neurons in each layer can be arbitrarily determined, the input layer and the output layer may include one or more units to represent the input pattern and the output pattern of the problem to be solved, respectively. The neural networks have been used to achieve the calculation of differentiated objects or event classification methods. The neural network is first trained by a known data representation related to object or event classification, and then used to distinguish unknown objects or event categories. The neural network is then trained by a data set containing the general set of data. The trained network will function as a general neural network model. In some embodiments, a local neural network model is achieved using a special set of training data and functions partially dependent upon the general neural network model.

Figure 11:
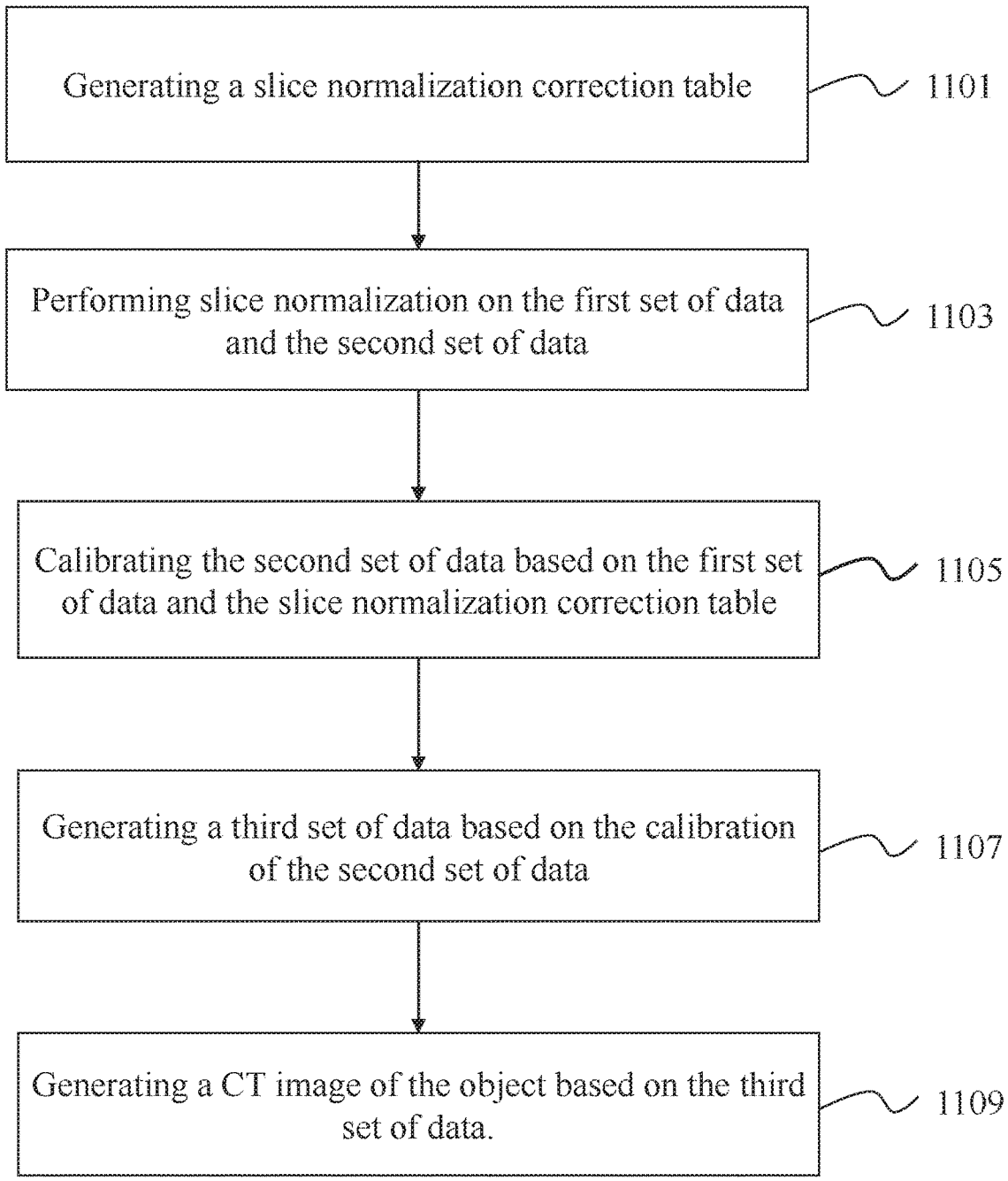
FIG. 11 is a flowchart illustrating an exemplary process of a slice normalization correction according to some embodiments of the present disclosure.

FIG. 11 is a flow chart illustrating an exemplary process of a slice normalization correction according to some embodiments of the present disclosure.

In 1101, a slice normalization correction table is generated. The slice normalization correction table may be generated by the correction table generating unit 650. In some embodiments, the slice normalization correction may be generated in a scanning protocol the same with the air correction. The scanning protocol may include a plurality of parameters. Merely by way of example, the parameters may be with respect to a collimator aperture, a detector aperture, an X-ray tube voltage and/or current, a scan mode, a table index speed, a gantry speed, a reconstruction field of view (FOV), kernel, or the like, or any combination thereof. In some embodiments, the slice normalization correction table is generated by performing an air scanning. In some embodiments, the slice normalization correction table is generated for eliminating the difference of every slice of the detectors. The difference of every slice of the detectors is affected by a plurality of factors of the detectors: The factors may include the position of the detectors, the angle of the detector. The slice normalization correction table may be updated after a period of time. In some embodiments, the slice normalization correction table include the return value of the edge detectors, the intensity of the X-ray, etc.

In 1103, a slice normalization is performed on the first set of data and the second set of data.

In 1105, the second set of data is calibrated based on the first set of data based on the slice normalization result and the slice normalization correction table by the neural network. In some embodiments, the calibrating may be implemented by an algorithm as an example:

$$(\mu D)_{obj} = (A_{DTC\_obj} A_{ALT\_obj}) - (A_{DTC\_air} - A\_ALT\_air) \quad (4)$$

$$A_{ALT} = f(A_{DTC\_obj}, A_{DTC\_air}, mA, \ldots) \quad (5)$$

wherein ADTC-obj is the return value of the detectors across the object, ADTC-air is the air correction table, $A_{REF-obj}$ is the return value of the reference detectors across the object, $A_{REF-air}$ is the return value of the reference detectors across the air, $A_{ALT-slice}$ is the return value of the edge detectors across the air, mA is the intensity of the X-ray across the air, f is a deep learning neural network.

In some embodiments, the input layers of the neural network may be configured to input data. The data may include the return value of the detectors $A_{DTC-obj}$, the air correction table $A_{REF-air}$, the intensity of the X-ray and/or other scanning data. The hidden layers may be configured to process the data from the input layers. The output layers may be configured to output the processed data from the hidden layers. The output data may include reference values (e.g. $A_{ALT-slice}$). The neural network may include a deep learning neural network model. The deep learning neural network model may be trained using a plurality of training data associated with at least one detector of the CT imaging system. The plurality of training data includes a set of data covering the return values of desired reference detectors and the edge detectors under each of the scan protocol required. In some embodiments, the plurality of training data may be obtained through experiments and/or computational simulation. Simulation of the return values of desired edge detectors fluctuation may be added into the plurality of training data to form a new set of data. The new set of data may be a new training data for the neural network. The goal of the deep learning neural network is to minimize the value of the $\min \|\{y_i\} - \{y_i\}_0\|$, wherein the $\{y_i\}_0$ are the return values of desired edge detectors.

In 1107, a third set of data based on the calibration of the second set of data is generated. The first set of data associated with air in a scanning area may be subtracted from the second set of data associated with an object in the scanning area to obtain the third set of data.

In 1109, a CT image of the object is generated based on the third set of the data. This step is the same with step 711 which may be a reference.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, 1101 may be omitted and the slice normalization table may be input by users.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device" or "system." Furthermore, aspects of the present disclosure may take the form of a computer program product embodied in one or more non-transitory computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, VB.NET, Python or the like, conventional procedural programming languages, such as the "C" programming language, Visual Basic, Fortran 2003, Pert, COBOL 2002, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter lie in less than all features of a single foregoing disclosed embodiment.

I claim:

1. A method for air calibration in a Computed Tomography (CT) imaging system implemented on at least one computing device each of which has at least one processor and storage, the method comprising:
    obtaining a set of data associated with an object in a scanning area;
    obtaining a neural network model;
    generating, based on the set of data associated with the object, one or more reference values using the neural network model;
    calibrating the set of data associated with the object using the one or more reference values to generate a set of calibrated data;
    and
    generating a CT image of the object based on the set of calibrated data.

2. The method of claim 1, wherein the neural network model includes a deep learning neural network model.

3. The method of claim 1, wherein the neural network model is trained using a plurality of training data associated with at least one detector of the CT imaging system.

4. The method of claim 3, wherein the plurality of training data is obtained via the at least one detector with respect to a plurality of scanning protocols.

5. The method of claim 1, wherein the neural network model includes at least three layers.

6. The method of claim 1, wherein the one or more reference values generated by the neural network model are view-dependent.

7. The method of claim 1, wherein the one or more reference values generated by the neural network model are slice-dependent.

8. The method of claim 1, wherein the generating, based on the set of data associated with the object, using the neural network model includes:
    obtaining a set of data associated with air in the scanning area; and
    generating, based on the set of data associated with air and the set of data associated with the object, the one or more reference values using the neural network model.

9. The method of claim 8, further comprising:
    obtaining one or more scanning parameters for the set of data associated with the object; and
    inputting the set of data associated with air, the set of data associated with the object, and the one or more scanning parameters into the neural network model to generate the one or more reference values.

10. The method of claim 1, wherein the calibrating the set of data associated with the object using the one or more reference values to generate a set of calibrated data includes:
    performing, based on the one or more reference values, an air calibration on the set of data associated with the object.

11. The method of claim 10, wherein calibrating the set of data associated with the object using the one or more reference values to generate a set of calibrated data further comprises:

performing the slice normalization on the set of data associated with the object using the one or more reference values.

12. The method of claim 1, wherein the calibrating the set of data associated with the object using the one or more reference values to generate a set of calibrated data includes:
performing, based on the one or more reference values, a slice normalization calibration on the set of data associated with the object.

13. A CT imaging system, comprising:
a computer-readable storage medium storing a first set of instructions for calibrating data;
at least one processor in communication with the computer-readable storage medium, wherein when executing the first set of instructions, the at least one processor is directed to:
obtain a set of data associated with an object in a scanning area;
obtain a neural network model;
generate, based on the set of data associated with the object, one or more reference values using the neural network model;
calibrate the set of data associated with the object using the one or more reference values to generate a set of calibrated data;
and
generate a CT image of the object based on the set of calibrated data.

14. The system of claim 13, wherein to generate, based on the set of data associated with the object, using the neural network model, the at least one processor is directed to:
obtain a set of data associated with air in the scanning area; and
generate, based on the set of data associated with air and the set of data associated with the object, the one or more reference values using the neural network model.

15. The system of claim 13, wherein the at least one processor is directed to:
obtain one or more scanning parameters for the set of data associated with the object; and
input the set of data associated with air, the set of data associated with the object, and the one or more scanning parameters into the neural network model to generate the one or more reference values.

16. The system of claim 13, wherein to calibrate, the set of data associated with the object using the one or more reference values to generate a set of calibrated data, the at least one processor is directed to:
perform, based on the one or more reference values, an air calibration on the set of data associated with the object.

17. The system of claim 13, wherein to calibrate the set of data associated with the object using the one or more reference values to generate a set of calibrated data, the at least one processor is directed to:
perform, based on the one or more reference values, a slice normalization calibration on the set of data associated with the object.

18. The system of claim 17, wherein to calibrate the set of data associated with the object using the one or more reference values to generate a set of calibrated data, the at least one processor is directed to:
performing a slice normalization on the set of data associated with the object using the one or more reference values.

19. A non-transitory computer readable medium storing executable instructions that, when executed by at least one processor, cause the at least one processor to effectuate a method comprising:
obtaining a set of data associated with an object in a scanning area;
obtaining a neural network model;
generating, based on the set of data associated with the object, one or more reference values using the neural network model;
calibrating the set of data associated with the object using the one or more reference values to generate a set of calibrated data;
and
generating a CT image of the object based on the set of calibrated data.

20. The non-transitory computer readable medium of claim 19, wherein the executable instructions, when executed by at least one processor, cause the at least one processor to effectuate a method comprising:
obtaining a set of data associated with air in the scanning area; and
generating, based on the set of data associated with air and the set of data associated with the object, the one or more reference values using the neural network model.

* * * * *